United States Patent [19]

Berger et al.

[11] 4,029,781
[45] June 14, 1977

[54] 1,4-DITHIIN (AND OXATHIIN)-YL CEPHALOSPORIN DERIVATIVES, AND COMPOSITIONS CONTAINING THEM

[75] Inventors: Christian Berger, Le Plessis Robinson; Daniel Farge, Thiais; Georges Gros, Bourg-La-Reine; Mayer Naoum Messer, Bievres; Claude Moutonnier, Le Plessis-Robinson, all of France

[73] Assignee: Rhone-Poulenc Industries, Paris, France

[22] Filed: Sept. 26, 1975

[21] Appl. No.: 617,066

[30] Foreign Application Priority Data

Sept. 27, 1974 France .............................. 74.32701
July 21, 1975 France .............................. 75.22682

[52] U.S. Cl. ............................ 424/246; 260/243 C; 260/327 P; 260/468 J
[51] Int. Cl.² ............. C07D 501/22; C07D 501/34; A61K 31/54
[58] Field of Search ................ 260/243 C; 424/246

[56] References Cited
UNITED STATES PATENTS

| | | |
|---|---|---|
| 3,516,997 | 6/1970 | Takano et al. ................. 260/243 C |
| 3,692,779 | 9/1972 | Holdrege ....................... 260/243 C |
| 3,886,151 | 5/1975 | Wei ................................ 260/243 C |
| 3,891,629 | 6/1975 | Diassi et al. ................... 260/243 C |

*Primary Examiner*—Donald G. Daus
*Assistant Examiner*—David E. Wheeler
*Attorney, Agent, or Firm*—Stevens, Davis, Miller & Mosher

[57] ABSTRACT

New cephalosporin compounds of the formula:

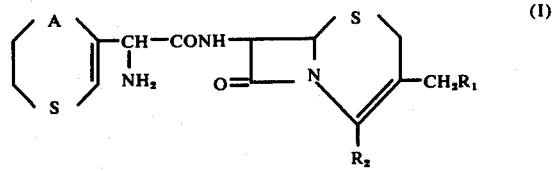

in which A is oxygen or sulphur, $R_1$ is hydrogen or acetoxy and $R_2$ is carboxy or a radical of the formula:

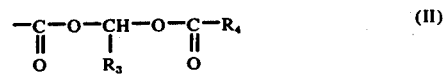

in which the radical

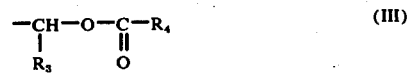

is a radical which can be easily removed enzymatically, and in which $R_3$ is hydrogen or straight or branched chain $C_{1-4}$ alkyl and $R_4$ is straight or branched chain $C_{1-4}$ alkyl or cyclohexyl, together with its diastereoisomeric forms and mixtures thereof, its acid addition salts and, where appropriate, its pharmaceutically acceptable non-toxic metal salts and addition salts with nitrogen-containing bases other than ammonia, exhibit valuable anti-bacterial properties, in particular against Gram-positive and Gram-negative bacteria.

13 Claims, No Drawings

1,4-DITHIIN (AND OXATHIIN)-YL CEPHALOSPORIN DERIVATIVES, AND COMPOSITIONS CONTAINING THEM

The present invention relates to cephalosporin derivatives, to their preparation and to compositions containing them.

The present invention provides cephalosporin derivatives of the formula:

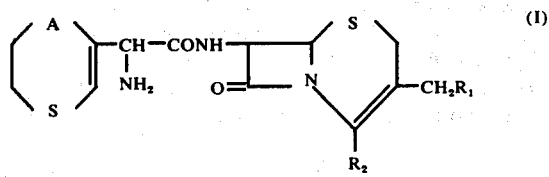

in which A represents oxygen or sulphur, $R_1$ represents hydrogen or acetoxy, and $R_2$ represents carboxy or a radical of the formula:

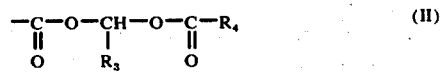

in which the radical

is a radical which can be easily removed enzymatically, and in which $R_3$ represents hydrogen or straight or branched chain $C_{1-4}$ alkyl, and $R_4$ represents straight or branched chain $C_{1-4}$ alkyl or cyclohexyl, their diastereoisomeric forms and mixtures thereof, their pharmaceutically acceptable acid addition salts and, when $R_2$ represents carboxy, their pharmaceutically acceptable non-toxic metal salts and addition salts with nitrogen-containing bases other than ammonia.

According to another aspect of the invention, the cephalosporins of the formula (I) can be obtained by reacting an acid of the formula:

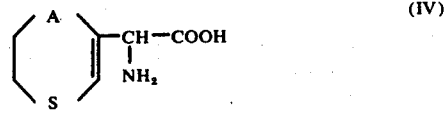

in which A is as defined above, the said acid being in its racemic or optically active form, and in which the amino group has been protected beforehand, or a reactive derivative of this acid, with a cephalosporin of the formula:

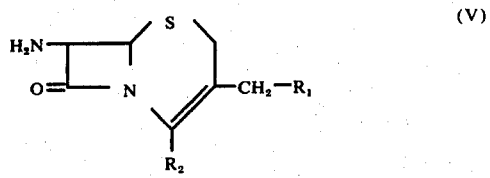

in which $R_1$ and $R_2$ are as defined above.

The acids of the formula (IV) are described and claimed in our copending U.S. Pat. application Ser. No. 616,991, filed on even date herewith.

If the free acid of the formula (IV) is used, the amino group can be protected by any method known per se for protecting an amino group without affecting the remainder of the molecule. It is necessary to protect the amino group with a group which can be easily removed. It is particularly advantageous to use the tertiary butoxycarbonyl group, which can be introduced by the action of tert.-butoxycarbonyl azide, tertiary butyl chloroformate or a mixed tertiary butyl and p-nitrophenyl carbonate.

If $R_2$ represents carboxy, the reaction of the acid of the formula (IV), in which the amino group has been protected, is generally carried out with a cephalosporin derivative of the formula (V) in which the carboxy group has been protected beforehand with a group which can be easily removed such as a tertiary butyl radical or a 2,2,2-trichloroethyl radical.

In general, the reaction is carried out in an organic solvent such as dimethylformamide or chloroform, in the presence of a condensation agent such as dicyclohexylcarbodiimide, at a temperature of from 0° to 40° C, and the groups which protect the amino and carboxy groups are then removed. This removal depends on the nature of the protective groups, and can be effected in a single stage or in two stages. If the removal is carried out in two stages, it is preferable first to remove the group which protects the carboxy group and then the group which protects the amino group.

If the amino protecting group is tertiary butoxycarbonyl and the carboxy protecting group is tertiary butyl, their replacement by a hydrogen atom can be carried out in a single stage by treatment in an acid medium. Preferably, trifluoroacetic acid is used and the process is carried out at a temperature of about 20° C. Under these conditions, the cephalosporin of the formula (I) is obtained as the trifluoroacetate salt from which the amino group can be liberated by any method known per se for obtaining an amine from one of its salts without affecting the remainder of the molecule.

If the amino protecting group is tertiary butoxycarbonyl and the carboxy protecting group is 2,2,2-trichloroethyl, the latter is first replaced by a hydrogen atom by treatment with zinc in acetic acid, and the tertiary butoxycarbonyl radical is then replaced by a hydrogen atom by treatment in an acid medium, preferably by treatment with trifluoroacetic acid. Under these conditions, the cephalosporin of the formula (I) is obtained as the trifluoroacetate salt and the free amine can be liberated from its salt under the conditions described above.

If, in the cephalosporin of formula (V), $R_2$ represents a radical of the formula (II) as defined above, the reaction of the free acid of the formula (IV) with the cephalosporin of the formula (V) is generally carried out in an organic solvent such as dimethylformamide or chloroform, in the presence of a condensation agent, such as dicyclohexylcarbodiimide, at a temperature of from 0° to 40° C, and the amino protecting group is then removed under the conditions described above.

The acid of the formula (IV) can also be used in the form of a reactive derivative, such as the acid halide, anhydride or mixed anhydride. It is particularly advantageous to employ the acid chloride. Under these conditions, the hydrochloride of the chloride of the acid of the formula (IV) is reacted with a cephalosporin derivative of the formula (V), in which $R_2$ is as defined above. When the acid of formula (IV) is employed in the form of a reactive derivative, it is not necessary to protect $R_2$ when it is carboxy. In general, this reaction is carried out in an organic solvent such as chloroform in the presence of an acid acceptor such as a nitrogen-containing organic base such as pyridine or triethylamine, or in an aqueous-organic medium, in the presence of an alkaline condensation agent such as sodium bicarbonate, at a temperature of from −20° to +20° C.

The acid of the formula (IV) can be obtained by saponifying the corresponding ester of the formula:

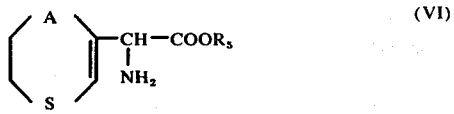
(VI)

in which A represents oxygen or sulphur and $R_5$ represents alkyl of 1 to 4 carbon atoms, using the customary conditions for the saponification of an ester to the corresponding acid.

In general, the ester to be saponified is treated with an alkali metal hydroxide in an aqueous-alcoholic medium at a temperature of from 0° to 50° C. Preferably, the methyl or ethyl ester is used and the saponification is carried out in an aqueous-methanolic medium at a temperature of about 5° C.

The ester of the formula (VI) can be obtained by reducing an oxime of the formula:

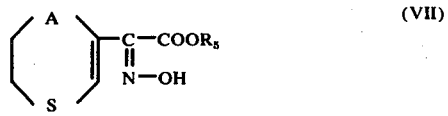
(VII)

in which A and $R_5$ are as defined above. In general, the reduction is performed using zinc in an aqueous-organic medium such as a mixture of methanol, formic acid and water, at a temperature from 0° to 25° C.

The oxime of the formula (VII) can be obtained by reacting a compound of the formula:

$$HA - CH_2CH_2 - SH \quad (VIII)$$

in which A is as defined above, with an ester of the formula:

(IX)

in which $R_5$ is as defined above and X represents halogen, preferably chlorine, the reaction taking place via a product of the formula:

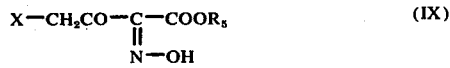
(X)

in which A and $R_5$ are as defined above, which is subsequently cyclised.

The reaction of the compound of the formula (VIII) with the ester of the formula (IX) is generally carried out in an organic solvent such as chloroform in the presence of an acid acceptor such as triethylamine, at a temperature of about 20° C.

The cyclisation of the ester of the formula (X) to the oxime of the formula (VII) is generally carried out by heating in an organic solvent such as benzene or toluene in the presence of a catalyst such as p-toluene-sulphonic acid, whilst removing the water at the rate at which it is formed.

The ester of the formula (IX) can be obtained by the method described by M. Hatanaka and T. Ishimaru, J. Med. Chem., 16, 978, (1973).

The optically active forms of the acid of the formula (IV) can be obtained either by chemical methods or enzymatic methods. For example, the D-form of the acid of the formula (IV) can be obtained by treating the racemic form with (+)-camphorsulphonic acid in an organic solvent such as an alcohol, for example methanol or ethanol, to give the salt of the D-form, purifying this salt by recrystallisation and liberating the free acid from this salt. The L-form of the acid of the formula (IV) can be obtained, for example, by selective enzymatic desacetylation of an acid of the formula:

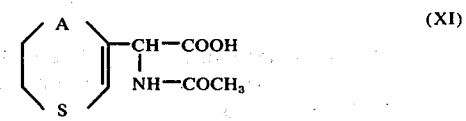
(XI)

in which A is as defined above.

The treatment of the racemic form of the acid of the formula (XI) with an amino-acylase gives the L-form of the acid of the formula (IV) and the D-form of the acid of the formula (XI).

Preferably, the selective desacetylation is carried out by an Aspergillus amino-acylase, at a pH of about 8 and a temperature of about 37° C.

The acid of the formula (XI) can be obtained according to one of the following processes:

a. By acetylation of the acid of the formula (IV), for example with acetyl chloride or acetic anhydride, or b. by saponification or hydrolysis of the corresponding ester, preferably the corresponding methyl or ethyl ester.

The methyl or ethyl ester of the acid of the formula (XI) can be obtained by reaction of a compound of the formula (VIII) with an ester of the formula:

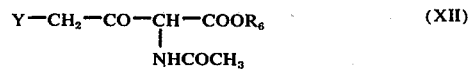
(XII)

in which Y represents halogen, preferably bromine, and $R_6$ represents methyl or ethyl, the reaction taking place via a product of the formula:

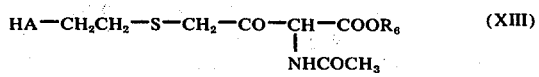
(XIII)

in which A and $R_6$ are as defined above, which is subsequently cyclised.

In general, the condensation of the compound of the formula (VIII) with the ester of the formula (XII) is carried out in an organic solvent such as chloroform in the presence of an acid acceptor such as triethylamine at a temperature of about 20° C.

The cyclisation of the product of the formula (XIII) to give an ester of the acid of the formula (XI) is generally carried out by heating in an organic solvent such as benzene or toluene in the presence of a catalyst such as p-toluenesulphonic acid, with removal of the water at the rate at which it is formed.

The ester of the formula (XII) can be obtained in accordance with the method of M. Hatanaka and T. Ishimaru, J. Med. Chem., 16, 978 (1973).

The product of the formula (V) in which $R_1$ represents hydrogen and $R_2$ represents carboxy is 7-amino-3-desacetoxy-cephalosporanic-acid (or 7-ADCA), which can be obtained either from a penicillin in accordance with the process described in Belgian Pat. No. 747,382 or by desacetoxylation of a product of the formula (V) in which $R_1$ represents acetoxy, in accordance with the process described in Belgian Pat. No. 779,034.

The compound of the formula (V) in which $R_1$ represents acetoxy and $R_2$ represents carboxy is 7-aminocephalosporanic acid (or 7-ACA) which can be obtained in accordance with the process described in Belgian Pat. No. 615,955 or in U.S. Pat. No. 3,239,394.

The compound of the formula (V) in which $R_1$ is as defined above and $R_2$ represents a radical of the formula (II), in which $R_3$ and $R_4$ are as defined above, can be prepared from a compound of the formula (V), in which $R_1$ is as defined above and $R_2$ represents carboxy, by any method known per se for the preparation of an ester from an acid without affecting the remainder of the molecule.

In general, an alkali metal salt or a tertiary amine salt, of a compound of the formula (V), in which $R_1$ is defined as above and $R_2$ represents carboxy, is reacted with a halide of the formula:

(XIV)

in which $R_3$ and $R_4$ are as defined above and Z represents halogen, in an inert solvent such as dimethylformamide, at a temperature of from 0° to 30° C.

The compounds of the formula (XIV) can be prepared in accordance with the method described in German Patent Application No. 2,350,230.

According to the invention, the cephalosporins of the formula (I) in which $R_1$ is as defined above and $R_2$ represents a radical of the general formula (II), in which $R_3$ and $R_4$ are as defined above, can also be obtained by esterifying a cephalosporin of the formula (I) in which $R_1$ is as defined above and $R_2$ represents carboxy, and in which the amino group has been protected beforehand by any method known per se for preparing an ester from an acid without affecting the remainder of the molecule.

In general, an alkali metal salt or a tertiary amine salt of a cephalosporin of the formula (I) as defined above, in which the amino group has been protected beforehand, is reacted with a halide of the formula (XIV) in which $R_3$, $R_4$ and Z are as defined above. Preferably, the reaction is carried out in an inert solvent such as dimethylformamide, at a temperature of from 0° to 30° C, and the amino protecting group is then removed by any method known per se for obtaining an amine from one of its salts without affecting the remainder of the molecule.

The cephalosporins of the formula (I) can be purified, if desired, by physical methods such as crystallisation or chromatography.

The cephalosporins of the formula (I) can be converted into acid addition salts. According to the processes of the present invention, the cephalosporins of the formula (I) are generally obtained as the trifluoroacetate salts which can be liberated and converted into other salts in accordance with the customary methods.

The cephalosporins of the formula (I) in which $R_2$ represents carboxy can also be converted into metal salts or addition salts with nitrogen-containing bases other than ammonia, in accordance with methods known per se. These salts can be obtained by reacting an alkali metal base or alkaline earth metal base, or an amine with a cephalosporin of the formula (I) in a suitable solvent such as an alcohol, an ether or water, or by exchange reaction with a salt of an organic acid. The salt formed precipitates, if necessary after concentrating its solution, and is isolated by filtration, decantation or lyophilisation.

The cephalosporin derivatives of the formula (I) and their salts have particularly valuable anti-bacterial properties. They exhibit a remarkable activity against Gram-positive and Gram-negative bacteria in vitro and in vivo.

In vitro, the products have proved active at concentrations of between 1 and 60 $\mu$g/cc. against strains of Staphylococci which are sensitive to penicillin G (*Staphylococcus aureus* 209 P and *Staphylococcus aureus* Smith) or at concentrations of between 1 and 50 $\mu$g/cc. against strains of Staphylococci resistant to penicillin G (*Staphylococcus aureus* MB 9) or at concentrations of between 1 and 100 $\mu$g/cc, against *Escherichia coli*, Monod strain.

In vivo, the products have proved active against experimental infections of mice with *Staphylococcus aureus* Smith (sensitive to penicillin G) at doses of between 0.05 and 5 mg/kg per day administered subcutaneously or between 0.05 and 30 mg/kg per day administered orally, or with *Escherichia coli* at doses of between 1 and 50 mg/kg per day administered subcutaneously or between 5 and 500 mg/kg per day administered orally.

Particularly interesting cephalosporins are those of the formula:

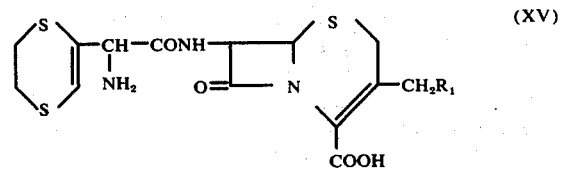

(XV)

in which $R_1$ represents hydrogen or acetoxy, which have been derived from the D, L and DL forms of the acid of the formula (IV) in which A represents sulphur and which are in a diastereoisomeric form or in the form of a mixture of diastereoisomers.

The following Examples illustrate the invention; percentages are by weight.

EXAMPLE 1

Dicyclohexylcarbodiimide (9.20 g.) is added to a solution of DL-$\alpha$-tert.-butoxycarbonylamino(5,6-dihydro-1,4-dithiin-2-yl)acetic acid (11.5 g.) and 3-acetoxy-7-amino-2-tert.-butoxycarbonyl-8-oxo-5-thia-1-aza-bicyclo[4.2.0]oct-2-ene (12.9 g.) in anhydrous dimethylformamide (100 cc.). The reaction mixture is stirred for 30 minutes at a temperature of about 20° C, and the precipitate is then filtered off, ethyl acetate (300 cc.) is added to the filtrate and the organic phase is washed twice with water (1,000 cc.), with a 1% citric acid solution (500 cc.), then with a saturated sodium bicarbonate solution (300 cc.) and finally with water (500 cc.). The organic phase is dried over magnesium sulphate, treated with decolourising charcoal, filtered and concentrated to dryness under reduced pressure (20 mm.Hg). A residue (26 g.) is obtained, which is chromatographed on silica gel (300 g.). Elution is carried out with a mixture of ethyl acetate and cyclohexane (35–65 by volume) (2,000 cc.) and, after concentrating the solution, 3-acetoxy-7-[DL-α-tert.-butoxycarbonylamino(5,6-dihydro-1,4-dithiin-2-yl)-acetamido]-2-tert.-butoxycarbonyl-8-oxo-5-thia-1-azabicyclo[4.2.0]-oct-2-ene (19 g.) is obtained.

This product (19 g.) is dissolved in trifluoroacetic acid (100 cc.) and the solution is left for 15 minutes at a temperature of about 20° C; the trifluoroacetic acid is then driven off under reduced pressure (1 mm.Hg). The residue is dissolved in ethyl acetate (75 cc.) and isopropyl ether (100 cc.) is then added. A precipitate appears, which is filtered off. This gives 3-acetoxymethyl-7-[DL-α-amino(5,6-dihydro-1,4-dithiin-2-yl)acetamido]-2-carboxy-8-oxo-5-thia-1-aza-bicyclo[4.2.0]oct-2-ene trifluoroacetate (14.6 g.) in the form of a cream solid.

$[\alpha]_D^{20} = +29.2° \pm 0.9°$ ($c = 1$, dimethylformamide)

Analysis. Calculated %: C, 39.58; H, 3.75; F, 8.05; N, 7.91; O, 22.60; S, 18.11. Found: C, 39.8; H, 3.4; F, 8.4; N, 8.1; S, 18.4.

3-Acetoxymethyl-7-amino-2-tert.-butoxycarbonyl-8-oxo-5-thia-1-aza-bicyclo[4.2.0]oct-2-ene can be prepared in accordance with R. J. Stedman, J. Med. Chem., 9, 444 (1966).

DL-α-tert.-Butoxycarbonylamino(5,6-dihydro-1,4-dithiin-2-yl)acetic acid can be prepared in the following manner:

tert.-Butoxycarbonyl azide (14.3 g.) is added to a suspension of DL-α-amino(5,6-dihydro-1,4-dithiin-2-yl)acetic acid (9.55 g.) in dimethylformamide (150 cc.) and triethylamine (17.6 cc.). This suspension is stirred at 35° C., for 3 days. The reaction mixture has at that stage become homogeneous. Water (1,000 cc.) and a saturated sodium bicarbonate solution (100 cc.) are added and the mixture is washed twice with ethyl ether (300 cc.). The aqueous phase is brought to pH 3 by adding citric acid. The precipitate formed is filtered off, washed with water and recrystallised from acetonitrile (400 cc.). This gives DL-α-tert.-butoxycarbonyl(5,6-dihydro-1,4-dithiin-2-yl)acetic acid (12 g.) in the form of white crystals which melt at about 205° C, with decomposition.

tert.-Butoxycarbonyl azide can be prepared in accordance with L. A. Carpino, B. A. Carpino, P. J. Crowley, C. A. Giza and P. H. Terry, Org. Synth., 44, 15 (1964).

DL-α-Amino(5,6-dihydro-1,4-dithiin-2-yl)acetic acid can be prepared in the following manner:

Normal sodium hydroxide solution (820 cc.) is added to a solution of ethyl DL-α-amino(5,6-dihydro-1,4-dithiin-2-yl)acetate (150 g.) in methanol (1,500 cc.). The reaction mixture is left for 16 hours at a temperature of about 5° C, and is then concentrated to dryness under reduced pressure (20 mm.Hg). Water (500 cc.) is added to the residue obtained and the mixture is filtered over "Supercel". The yellow filtrate obtained is cooled in an ice bath and is acidified by adding 4N hydrochloric acid (600 cc.).

The acid solution is treated with decolourising charcoal, filtered and then brought to pH 4.5 by adding concentrated sodium hydroxide solution. The precipitate which has appeared is filtered off. This gives DL-α-amino(5,6-dihydro-1,4-dithiin-2-yl)acetic acid (99 g.) in the form of white crystals melting at about 260° C, with decomposition.

Ethyl DL-α-amino(5,6-dihydro-1,4-dithiin-2-yl) acetate can be prepared in the following manner:

50% formic acid (1,600 cc.) is added to a solution of ethyl α-hydroxyimino(5,6-dihydro-1,4-dithiin-2-yl) acetate (171 g.) in methanol (800 cc.). The mixture is cooled to 5° C, and zinc powder (135 g.) is then added in small portions in such a way that the temperature does not exceed 28° C. The mixture is then stirred at 5° C. for 30 minutes, after which it is filtered and the filtrate is concentrated under reduced pressure (20 mm.Hg) to a volume of about 1,000 cc. This residue is washed with methylene chloride (twice 200 cc.), water (1500 cc.) is added to the aqueous phase and the latter is neutralised by adding sodium carbonate until the pH is 8.9, in the presence of methylene chloride (500 cc.). The organic phase is separated off, the aqueous phase is washed with methylene chloride (500 cc.) and the organic extracts are combined, treated with decolourising charcoal and filtered. After concentration to dryness under reduced pressure (20 mm.Hg), ethyl DL-α-amino(5,6-dihydro-1,4-dithiin-2-yl)acetate (150 g.) is obtained in the form of a pale yellow oil.

Ethyl α-hydroxyimino(5,6-dihydro-1,4-dithiin-2-yl)acetate can be prepared in the following manner:

Ethyl 2-hydroxyimino-4-(2-mercapto-ethylthio)-3-oxo-butyrate (655 g.) is suspended in toluene (3,500 cc.) in the presence of p-toluenesulphonic acid monohydrate (22 g.). The mixture is heated under reflux (the water being separated off at the rate at which it is formed, in a Dean-Stark apparatus) for 40 minutes and is then cooled to 60° C., and concentrated to dryness under reduced pressure (20 mm.Hg). The residue is dissolved in ethyl acetate (200 cc.) and the solution obtained is washed twice with a saturated sodium bicarbonate solution (700 cc.) and then with water (twice 700 cc.), after which it is dried over magnesium sulphate and finally treated with decolourising charcoal. The solution is filtered and the filtrate is concentrated to dryness under reduced pressure (20 mm.Hg). The residue obtained is dissolved in hot chloroform (450 cc.) and carbon tetrachloride (800 cc.). The mixture is cooled to 0° C, for 16 hours and the crystals obtained are filtered off. This gives ethyl α-hydroxyimino(5,6-dihydro-1,4-dithiin-2-yl)-acetate (173 g.) in the form of white crystals melting at 142° C.

Ethyl 2-hydroxyimino-4-(2-mercapto-ethylthio)-3-oxo-butyrate can be prepared in the following manner:

A solution of ethyl 4-chloro-2-hydroxyimino-3-oxo-butyrate (1,050 g.) in chloroform (2,500 cc.) is added to a solution of ethanedithiol (900 cc.) and triethylamine (765 cc.) in chloroform (2,500 cc.), whilst keeping the temperature at 20° C. The mixture is left at 20° C. for 1 hour, normal hydrochloric acid (2,000 cc.) is then added, and the organic phase is separated off, washed twice with water (2,000 cc.) and then dried over magnesium sulphate. After filtration, the filtrate is concentrated to dryness under reduced pressure (20 mm.Hg). Methylene chloride (500 cc.) is added to the partially crystalline residue and the mixture is then cooled to −10° C. It is filtered and ethyl 2-hydroxyimino-4-(2-mercapto-ethylthio)-3-oxo-butyrate (655 g.) is obtained in the form of white crystals melting at 110° C.

Ethyl 4-chloro-2-hydroxyimino-3-oxo-butyrate can be prepared according to M. Hatanaka and T. Ishimaru, J. Med. Chem, 16, 978 (1973).

EXAMPLE 2

Dicyclohexylcarbodiimide (6.2 g.) is added to a solution of DL-α-tert.-butoxycarbonylamino(5,6-dihydro-1,4-dithiin-2-yl)acetic acid (8.15g) and 7-amino-3-methyl-8-oxo-2-(2,2,2-trichloro-ethoxycarbonyl)-5-thia-1-aza-bicyclo[4.2.0]oct-2-ene (9.55 g.) in dimethylformamide (120 cc.) and the mixture is stirred for 2 hours. It is then filtered; the filtrate is diluted with ethyl acetate (150 cc.) and washed with water (600 cc.), 4N hydrochloric acid (250 cc.), sodium bicarbonate (250 cc.) and distilled water (250 cc.). The organic phase is dried over magnesium sulphate, treated with decolourising charcoal, filtered and concentrated to dryness under reduced pressure (20 mm.Hg). This gives a residue (17.4 g.) which is chromatographed on silica gel (250 g.). 7-[DL-α-tert.-butoxycarbonylamino(5,6-dihydro-1,4-dithiin-2-yl)acetamido]-3-methyl-8-oxo-2-(2,2,2-trichloro-ethoxycarbonyl)-5-thia-1-aza-bicyclo[4.2.0]oct-2-ene (11.8 g.) is eluted with a 30–70 (by volume) mixture of ethyl acetate and cyclohexane (2,000 cc.) in the form of a pale yellow varnish.

Zinc powder (11.1 g.) is added to a solution of 7-[DL-α-tert.-butoxycarbonylamino(5,6-dihydro-1,4-dithiin-2-yl)acetamido]-3-methyl-8-oxo-2-(2,2,2-trichloro-ethoxycarbonyl)-5-thia-1-aza-bicyclo[4.2.-0]oct-2-ene (11.8 g.) in a mixture of dimethylformamide (60 cc.) and glacial acetic acid (30 cc.) cooled in an ice bath, and the whole is stirred for 3 hours. The reaction mixture is then filtered; ethyl acetate (200 cc.) is added to the filtrate and the mixture is washed with water (500 cc.). The aqueous phase is extracted with ethyl acetate (200 cc.); the organic phases are combined, washed with water (200 cc.) and then extracted twice with a saturated sodium bicarbonate solution (200 cc.). The alkaline solution is acidified to pH 2.5 by adding 4 N hydrochloric acid in the presence of ethyl acetate (200 cc.) and the organic fraction is washed with water (200 cc.), dried over magnesium sulphate, treated with decolourising charcoal, and filtered. The filtrate is concentrated to dryness under reduced pressure (20 mm.Hg). This gives 7-[DL-α-tert.-butoxycarbonylamino(5,6-dihydro-1,4-dithiin-2-yl)acetamido]-2-carboxy-3-methyl-8-oxo-5-thia-1-aza-bicyclo[4.2.0]oct-2-ene (8.5 g.) in the form of a colourless varnish.

7-[DL-α-tert.-Butoxycarbonylamino(5,6-dihydro-1,4-dithiin-2-yl)acetamido]-2-carboxy-3-methyl-8-oxo-5-thia-1-aza-bicyclo[4.2.0]oct-2-ene (8.5 g.) is dissolved in trifluoroacetic acid (80 cc.). The solution obtained is left standing for 10 minutes and the trifluoroacetic acid is then driven off under reduced pressure (1 mm. Hg). The residue obtained is dissolved in ethyl acetate (10 cc.) and ethyl ether (120 cc.) is added. A product precipitates and is filtered off. This gives 7-[DL-α-amino-(5,6-dihydro-1,4-dithiin-2-yl)-acetamido]-2-carboxy-3-methyl-8-oxo-5-thia-1-aza-bicyclo[4.2.0]oct-2-ene trifluoroacetate (6.8 g.) in the form of a white powder, $[\alpha]_D^{20} = +88.6° \pm 1.4°$ ($c = 1$, dimethylformamide).

Analysis. Calculated %: C, 38.9; H, 3.8; F, 10.2; N, 8.6; O, 18.8; S, 19.7. Found: C, 39.0; H, 4.1; F, 10.5; N, 8.4; S, 19.4.

7-Amino-3-methyl-8-oxo-2-(2,2,2-trichloro-ethoxycarbonyl)-5-thia-1-aza-bicyclo[4.2.0]oct-2-ene can be prepared according to R. R. Chauvette, P. A. Pennington, C. W. Ryan, R. D. G. Cooper, F. L. Jose, I. G. Wright, E. M. Van Heyningen and G. W. Huffman, J. Org. Chem. 36, 1259 (1971).

EXAMPLE 3

Following the procedure of Example 2, but starting from D-α-tert.butoxycarbonylamino(5,6-dihydro-1,4-dithiin-2-yl)acetic acid (5.2 g.) and 7-amino-3-methyl-8-oxo-2(2,2,2-trichloro-ethoxycarbonyl)-5-thia-1-aza-bicyclo[4.2.0]oct-2-ene (6.1 g.) in dimethylformamide (120 cc.), in the presence of dicyclohexylcarbodiimide (4.02 g.), 7-[D-α-tert.-butoxycarbonylamino(5,6-dihydro-1,4-dithiin-2-yl)acetamido]-3-methyl-8-oxo-2-(2,2,2-trichloroethoxycarbonyl)-5-thia-1-aza-bicyclo[4.2.0]oct-2-ene (5.2 g.) is obtained.

$[\alpha]_D^{20} = +45.6° \pm 1°$ ($c = 1$, chloroform)

On treating 7-[D-α-tert.-butoxycarbonylamino(5,6-dihydro-1,4-dithiin-2-yl)acetamido]-3-methyl-8 -oxo-2-(2,2,2-trichloro-ethoxycarbonyl)-5-thia-1-aza-bicyclo[4.2.0]oct-2-ene (5.2 g.) with zinc powder (5.05 g.) in dimethylformamide (30 cc.) and glacial acetic acid (15 cc.), 7-[D-α-tert.-butoxycarbonylamino(5,6-dihydro-1,4-dithiin-2-yl)acetamido]-2-carboxy-3-methyl-8-oxo-5-thia-1-aza-bicyclo[4.2.0]oct-2-ene (3.8 g.) is obtained in the form of a colourless varnish.

7-[D-α-tert.-Butoxycarbonylamino(5,6-dihydro-1,4-dithiin-2-yl)acetamido]-2-carboxy-3-methyl-8-oxo-5thia-1-aza-bicyclo[4.2.0]oct-2-ene (3.7 g.) is dissolved in trifluoroacetic acid (35 cc.) and this solution is stirred for 10 minutes at about 20° C. It is concentrated to dryness under reduced pressure (1 mm Hg), the residue is dissolved in ethyl acetate (6 cc.) and ethyl ether (70 cc.) is added. A precipitate forms which is filtered off. This gives 7-[D-α-amino(5,6-dihydro-1,4-di-thiin-2-yl)acetamido]-2-carboxy-3-methyl-8-oxo-5-thia-1-aza-bicyclo[4.2.0]oct-2-ene trifluoroacetate (1.8 g.) in the form of a white powder.

$[\alpha]_D^{20} = +119.2° \pm 1.8°$ ($c = 1$, dimethylformamide)

Analysis. Calculated %: C, 39.05; H, 3.75; F, 9.70; N, 8.75; O, 18.75; S, 20.00. Found: C, 38.7; H, 3.65; F, 9.7; N, 8.4; S, 19.8.

On following the procedure of Example 1, D-α-tert.-butoxycarbonylamino(5,6-dihydro-1,4-dithiin-2-yl)acetic acid (5.4 g.)

$[\alpha]_D^{20} = -109° \pm 2°$ ($c = 1$, dimethylformamide) is obtained by the action of tert.-butoxycarbonyl azide (8.6 g.) on D-α-amino(5,6-dihydro-1,4-dithiin-2-yl)acetic acid (5.5 g.) in dimethylformamide (100 cc.) containing triethylamine (10.5 cc.).

D-α-Amino(5,6-dihydro-1,4-dithiin-2-yl)acetic acid can be prepared in the following manner:

(+)-Camphorsulphonic acid (34.8 g.) is added to a suspension of DL-α-amino(5,6-dihydro-1,4-dithiin-2-yl)acetic acid (28.7 g.) in methanol (150 cc.). The mixture is heated gradually until dissolved and is then concentrated to dryness under reduced pressure (20 mm Hg). After five recrystallisations of the residue from a mixture of acetonitrile and water (90:10 by volume), the salt of (+)-camphorsulphonic acid with D-α-amino(5,6-dihydro-1,4-dithiin-2-yl)acetic acid (5.5 g.) is obtained in the form of white crystals.

$[\alpha]_D^{20} = -39.3° \pm 1°$ ($c = 1$, water)

This salt (3.5 g.) is dissolved in distilled water (50 cc.) and the pH is brought to 4 by adding sodium bicarbonate. The solution is concentrated under reduced pressure (20 mm Hg) to a volume of 20 cc. and left for 20 hours at 4° C. The precipitate formed is filtered off.

This gives D-α-amino(5,6-dihydro-1,4-dithiin-2-yl)acetic acid (1.3 g.) in the form of white crystals.

$[\alpha]_D^{20} = -138° \pm 1.6°$ ($c = 1$, N hydrochloric acid).

EXAMPLE 4

7-Amino-3-methyl-8-oxo-2-(2,2,2-trichloroethoxycarbonyl)-5-thia-1-aza-bicyclo[4.2.0]oct-2-ene (17.6 g.) and dicyclohexylcarbodiimide (11.5 g.) are added to a solution of DL-α-tert.-butoxycarbonylamino(5,6-dihydro-1,4-oxathiin-2-yl)acetic acid (14 g.) in chloroform (120 cc.) and the mixture is stirred for 12 hours at a temperature of about 20° C. The reaction mixture is then filtered and the filtrate is concentrated under reduced pressure (20 mm Hg). A gummy residue is obtained, which is dissolved in ethyl acetate (250 cc.); the solution is washed twice with 2 N hydrochloric acid (a total of 200 cc.), then twice with a saturated sodium bicarbonate solution (a total of 200 cc.) and finally twice with water (a total of 200 cc.). The oganic phase is dried over magnesium sulphate, treated with decolourising charcoal, filtered and then concentrated under reduced pressure (20 mm Hg). A residue (35 g.) is obtained, which is chromatographed on silica (350 g.).

Elution is carried out successively with a mixture of ethyl acetate and cyclohexane (1:9 by volume) (400 cc.) and then with a mixture of ethyl acetate and cyclohexane (15:85 by volume) (800 cc.). The corresponding eluates are discarded. Thereafter elution is carried out with a mixture of ethyl acetate and cyclohexane (15-85 by volume) (1,400 cc.).

These eluates are concentrated to dryness under reduced pressure (20 mm Hg). This gives 3-methyl-8-oxo-7-[DL-α-tert.-butoxycarbonylamino(5,6-dihydro-1,4-oxathiin-2-yl)acetamido]-2-(2,2,2-trichloro-ethoxycarbonyl)-5-thia-1-aza-bicyclo[4.2.0]oct-2-ene (23.5 g.) in the form of an amorphous white powder.

3-Methyl-8-oxo-7-[DL-α-tert.-butoxycarbonylamino(5,6-dihydro-1,4-oxathiin-2-yl)acetamido]-2-(2,2,2-trichloroethoxycarbonyl)-5-thia-1-aza-bicyclo[4.2.0]oct-2-ene (23.4 g.) is dissolved in dimethylformamide (135 cc.) and acetic acid (40 cc.). Zinc powder (22 g.) is added to this solution and the mixture is stirred for 3 hours at about 20° C. It is filtered through Supercel and the solution is then concentrated under reduced pressure (0.1 mm Hg)). An oil is obtained, which is taken up in water (800 cc.) and extracted twice with ethyl acetate (a total of 400 cc.). The organic phase is treated twice with a saturated sodium bicarbonate solution (a total of 400 cc.) and the aqueous fraction is acidified in the presence of ethyl acetate (200 cc.) by adding 4 N hydrochloric acid until the pH is 2.5. The organic phase is decanted, washed with water (100 cc.), dried over magnesium sulphate, treated with decolourising charcoal, filtered and concentrated under reduced pressure (20 mm Hg). 2-Carboxy-3-methyl-8-oxo-7-[DL-α-tert.-butoxycarbonylamino(5,6-dihydro-1,4-oxathiin-2-yl)acetamido]-5-thia-1-aza-bicyclo[4.2.0]-oct-2-ene (13.9 g.) is obtained in the form of an amorphous white powder.

2-Carboxy-3-methyl-8-oxo-7-[DL-αtert.-butoxycarbonylamino(5,6-dihydro-1,4-oxathiin-2-yl)acetamido]-5-thia-1-aza-bicyclo[4.2.0]oct-2-ene (13.8 g.) is dissolved in trifluoroacetic acid (139 cc.). The reactants are left in contact for 15 minutes, whilst stirring, at a temperatue of about 0° C. They are then concentrated to dryness under reduced pressure (1 mm Hg) and the residue is taken up in ethyl acetate (100 cc.) and again concentrated to dryness under reduced pressure (1 mm Hg). The residue obtained is dissolved in ethyl acetate (100 cc.) and this solution is then poured into ethyl ether (300 cc.); a product precipitates. The precipitate is washed twice by decanting using ethyl ether (a total of 600 cc.) and is then isolated by filtration. This gives 7-[DL-α-amino(5,6-dihydro-1,4-oxathiin-2-yl)acetamido]-2-carboxy-3-methyl-8-oxo-5-thia-1-aza-bicyclo[4.2.0]oct-2-ene trifluoroacetate (11.4 g.).

$[\alpha]_D^{20} = +114.2° \pm 1.7°$ ($c = 1.3$, dimethylformamide).

Analysis. Calculated %: C, 39.59; H, 3.73; F, 11.75; N, 8.65; O, 27.03; S, 13.21. Found: C, 40.3; H, 3.7; F, 10.5; N, 8.8; S, 13.4.

The DL-α-tert.-butoxycarbonylamino(5,6-dihydro-1,4-oxathiin-2-yl)acetic acid starting material can be prepared in the following manner:

DL-α-Amino(5,6-dihydro-1,4-oxathiin-2-yl)acetic acid (25.4 g.) is suspended in dimethylformamide (435 cc.); tert.-butoxycarbonyl azide (41.5 g.) and triethylamine (51 cc.) are added. The reactants are left in contact for 48 hours whilst stirring at a temperature of 35° C. The solution is concentrated under reduced pressure (1 mm Hg), the residue is taken up in water (300 cc.) and the pH is adjusted to 8.5 by adding a saturated sodium bicarbonate solution. The aqueous phase is extracted twice with ethyl ether (a total of 500 cc.), which is removed, and is then acidified to pH = 3 by adding 4 N hydrochloric acid. A product precipitates, which is filtered off and then dissolved in methylene chloride (600 cc.). The solution obtained is dried over magnesium sulphate, filtered and concentrated to dryness under reduced pressure (20 mm Hg). This gives DL-α-tert.-butoxycarbonylamino(5,6-dihydro-1,4-oxathiin-2-yl)acetic acid (26.2 g.) melting at 160° C.

DL-α-amino(5,6-dihydro-1,4-oxathiin-2-yl)acetic acid can be prepared in the following manner:

Ethyl DL-α-amino(5,6-dihydro-1,4-oxathiin-2-yl)acetate (37 g.) is dissolved in methanol (350 cc.) and N sodium hydroxide solution (182 cc.) is then added. The reactants are left in contact for 3 hours at a temperature of about 4° C and the solution is then concentrated under reduced pressure (20 mm Hg) to about ⅓ of the initial volume. It is acidified to pH 4.5 by adding 4 N hydrochloric acid at a temperature of about 5° C. A product crystallises. The mixture is stirred for 15 minutes and the precipitate is then filtered off; this gives DL-α-amino(5,6-dihydro-1,4-oxathiin-2-yl)acetic acid (19.4 g.) in the form of white crystals melting at about 270° C.

Ethyl DL-α-amino(5,6-dihydro-1,4-oxathiin-2-yl)acetate can be prepared in the following manner:

Ethyl α-hydroxyimino(5,6-dihydro-1,4-oxathiin-2-yl)acetate (295 g.) is dissolved in methanol (1.5 liters) and formic acid (1.5 liters) and water (1.5 liters) are then added. The mixture is cooled in a bath of ice and water and zinc powder (250 g.) is added in small portions over the course of 30 minutes. The reactants are left in contact for 2 hours whilst stirring at a temperature of about 20° C, the mixture is then filtered and the solution is concentrated under reduced pressure (20 mm Hg) to a volume of 1 liter. Water (1.5 liters) is added and the mixture is extracted twice with ethyl acetate (a total of 3 liters). The organic extracts are removed and the aqueous phase is brought to pH 10 by adding sodium hydroxide solution and is then extracted three times with methylene chloride (a total of 1.5 liters). The organic extracts are combined, dried over sodium sulphate, treated with decolourising charcoal, filtered and concentrated under reduced pressure (20 mm Hg). This gives ethyl DL-α-amino(5,6-dihydro-1,4-oxathiin-2-yl)acetate (150 g.) in the form of an oil.

Ethyl α-hydroxyimino(5,6-dihydro-1,4-oxathiin-2-yl)acetate can be prepared in the following manner:

Ethyl 4-(2-hydroxy-ethylthio)-2-hydroxyimino-3-oxobutyrate (321 g.) is dissolved in boiling toluene (3.2 liters) and para-toluenesulphonic acid monohydrate (26 g.) is then added. Vigorous boiling occurs, with liberation of water, which is removed in a Dean-Stark apparatus. The heating of the reaction mixture is continued for 15 minutes. After cooling, the toluene solution is filtered and washed three times with water (a total of 1.5 liters), then with a saturated sodium bicarbonate solution (200 cc.) and finally with water (500 cc.). It is dried over magnesium sulphate, treated with decolourising charcoal, filtered and concentrated to dryness under reduced pressure (20 mm Hg). Ethyl α-hydroxyimino(5,6-dihydro-1,4-oxathiin-2-yl)acetate (273 g.) is obtained in the form of an oil which slowly solidifies.

Ethyl 4-(2-hydroxy-ethylthio)-2-hydroxyimino-3-oxobutyrate can be prepared in the following manner:

Ethyl 4-chloro-2-hydroxyimino-3-oxo-butyrate (340 g.) is dissolved in chloroform (1.5 liters) and 2mercapto-ethanol (126 cc.) is then added. Triethylamine (248 cc.) dissolved in chloroform (1 liter) is added to the solution obtained, at about 20° C, over the course of 30 minutes. The reactants are left in contact for 15 hours whilst stirring at about 20° C. The reaction mixture is now washed with water (200 cc), then with 2 N hydrochloric acid (200 cc) and finally four times with water (a total of 1 liter). The organic phase is dried over sodium sulphate, treated with decolourising charcoal, filtered and concentrated to dryness under reduced pressure (20 mm Hg). This gives ethyl 4-(2-hydroxy-ethylthio)-2-hydroxyimino-3-oxo-butyrate (321 g.) in the form of an oil which slowly solidifies.

EXAMPLE 5

3-Acetoxymethyl-7-amino-8-oxo-2-tert.-butoxycarbonyl-5-thia-1-aza-bicyclo[4.2.0]oct-2-ene (11.2 g.) and dicyclohexylcarbodiimide (7.7 g.) are added to a solution of DL-60-tert.-butoxycarbonylamino(5,6-dihydro-1,4-oxathiin-2-yl)acetic acid (9.4 g.) in chloroform (85 cc.). The reactants are left in contact for 12 hours whilst stirring at a temperature of about 20° C and the solid formed is then filtered off. The filtrate is concentrated under reduced pressure (20 mm Hg) and the residue is dissolved in ethyl acetate (200 cc.). The solution is washed twich with 2 N hydrochloric acid (a total of 150 cc.) then twice with a saturated sodium bicarbonate solution (a total of 150 cc.) and finally twice with water (a total of 200 cc.). The organic phase is dried over sodium sulphate, treated with decolourising charcoal, filtered and then concentrated under reduced pressure (20 mm Hg). A residue (25 g.) is obtained, which is chromatographed over silica (250 g.). Elution is carried out successively with a mixture of ethyl acetate and cyclohexane (1:9 by volume) (120 cc.) followed by a mixture of ethyl acetate and cyclohexane (15:85 by volume) (360 cc.). The corresponding eluates are discarded. Elution is then carried out with a mixture of ethyl acetate and cyclohexane (35:65 by volume) (360 cc.). These eluates are concentrated to dryness under reduced pressure (20 mm Hg). 3-Acetoxymethyl-8-oxo-7-[DL-α-tert.-butoxycarbonylamino(5,6-dihydro-1,4-oxathiin-2-yl)acetamido]-2-tert.-butoxycarbonyl-5-thia-1-aza-bicyclo[4.2.0]oct-2-ene (12.8 g.) is obtained in the form of a white amorphous powder.

3-Acetoxymethyl-8-oxo-7-[DL-α-tert.-butoxycarbonylamino(5,6-dihydro-1,4-oxathiin-2-yl)acetamido]-2-tert.-butoxycarbonyl-5-thia-1-aza-bicyclo[4.2.0]oct-2-ene (12.7 g.) is dissolved in trifluoroacetic acid (120 cc.). The reactants are left in contact for 15 minutes whilst stirring at a temperature of about 20° C. The mixture is concentrated to dryness under reduced pressure (1 mm Hg), the residue is taken up in ethyl acetate (100 cc.) and the mixture is again concentrated to dryness under reduced pressure (1 mm Hg). The residue obtained is dissolved in ethyl acetate (25 cc.) and this solution is then poured into ethyl ether (100 cc.); a product precipitates. The precipitate is washed twice by decanting with ethyl ether (a total of 500 cc.) and is then isolated by filtration. This gives 3-acetoxymethyl-7-[DL-α-amino(5,6-dihydro-1,4-oxathiin-2-yl)acetamido]-2-carboxy-8-oxo-5-thia-1-aza-bicyclo[4.2.0 oct-2-ene trifluoroacetate (9.7 g.).

$[\alpha]_D^{20} = +24.0° + 0.8°$ ($c = 1$, dimethylformamide)

Analysis: Calculated %: C, 39.78; H, 3.71; F, 10.49; N, 7.73; O, 26.49; S, 11.80. Found: C, 40.2; H, 3.8; F, 9.8; N, 7.9; S, 11.8.

EXAMPLE 6

Dicyclohexylcarbodiimide (5.15 g.) is added to a solution of DL-α-tert.-butoxycarbonylamido(5,6-dihydro-1,4-dithiin-2-yl)acetic acid (6.1 g.) and 7-amino-3-methyl-8-oxo-2-pivaloyloxymethoxycarbonyl-5-thia-1-aza-bicyclo-[4.2.0]oct-2-ene (7.8 g.) in anhydrous dimethylformamide (75 cc.), whilst keeping the temperature at 5° C. The mixture is stirred for 2 hours at 5° C and then filtered; the precipitate is washed with ethyl acetate (250 cc.), the filtrate is washed with water (600 cc.) and the aqueous phase is extracted with ethyl acetate (250 cc.). The organic phases are combined, washed with a saturated sodium chloride solution (250 cc.); dried over magnesium sulphate and filtered in the presence of decolouring charcoal. After evaporating the ethyl acetate under reduced pressure (20 mm Hg), a yellow varnish is obtained, which is chromatographed on a columm containing silica gel (125 g.), elution being carried out with a 60:40 (by volume) mixture of ethyl acetate and cyclohexane; an eluate (500 cc.) is collected and is concentrated under reduced pressure. This gives 7-[DL-α-tert.-butoxycarbonylamino(5,6-dihydro-1,4-dithiin-2-yl)acetamido]-3-methyl-8-oxo-2-pivaloyloxymethoxycarbonyl-5-thia-1-aza-bicyclo[4.2.0]oct-2-ene (9 g.) in the form of a cream varnish.

This product is dissolved in trifluoroacetic acid (75 cc.) whilst stirring and the solution is left at 5° C for 45 minutes. The trifluoroacetic acid is driven off under reduced pressure (0.5 mm Hg) and the residue is suspended in isopropyl ether (100 cc.). The solid is filtered off, washed twice with isopropyl ether (500 cc.) and dried. This gives 7-[DL-α-amino(5,6-dihydro-1,4-dithiin-2-yl)acetamido]-3-methyl-8-oxo-2-pivaloyloxymethoxycarbonyl-5-thia-1-aza-bicyclo[4.2.0 oct-2-ene trifluoroacetate (8.5 g.) in the form of a pale yellow powder.

$[\alpha]_D^{20} = +55° \pm 1°$ ($c = 1$, dimethylformamide).

Analysis: Calculated %: C, 42.92; H, 4.58; F, 9.26; N, 6.83; O, 20.79; S, 15.62. Found: C, 43.4; H, 4.65; F, 9.3; N, 6.8; S, 15.3.

7-Amino-3-methyl-8-oxo-2-pivaloyloxymethoxycarbonyl-5-thia-1-aza-bicyclo[4.2.0]oct-2-ene can be prepared in accordance with the method described in German Patent Specification No. 1,951,012.

The present invention also provides pharmaceutical compositions, which are useful for therapeutic purposes, which contain as active ingredient, at least one cephalosporin of the formula (I) associated with one or more pharmaceutically acceptable carriers, diluents or adjuvants. These compositions can be administered orally, parenterally or rectally.

Tablets, pills, powders or granules can be used as solid compositions suitable for oral administration. In those compositions, an active ingredient according to the invention is mixed with one or more inert diluents or adjuvants such as sucrose, lactose or starch. These compositions can also contain substances other than the diluents, for example a lubricant such as magnesium stearate.

Pharmaceutically acceptable emulsions, solutions, suspensions, syrups and elixirs containing an inert diluent such as water or paraffin oil can be used as liquid compositions suitable for oral administration. These compositions can also contain substances other than the diluents, for example adjuvants, such as wetting agents, sweeteners or flavouring substances.

The compositions suitable for parenteral administration can be sterile aqueous or non-aqueous solutions, suspensions or emulsions. As the solvent or vehicle it is possible to use propylene glycol, polyethylene glycol, vegetable oils, in particular olive oil, and injectable organic esters, for example ethyl oleate. These compositions can also contain adjuvants, in particular wetting agents, emulsifiers or dispersing agents. Sterilisation can be carried out in various ways, for example by a bacteriological filter, by incorporating sterilising agents into the composition, by irradiation or by heating. They can also be prepared in the form of sterile solid compositions which can be dissolved in sterile water or any other injectable sterile medium at the time of use.

The compositions suitable for rectal administration are suppositories which can contain excipients such as cacao butter or suppository wax in addition to the active ingredient.

In human therapy, the compositions according to the invention are particularly useful in the treatment of infections of bacterial origin.

In general terms, the physician will decide the posology which he considers to be most appropriate in the light of the age, weight, degree of infection and other factors specific to the subject to be treated. In general, the doses for an adult patient are between 1 and 12 g per day of active ingredient administered orally, intramuscularly or intravenously.

The Examples which follow illustrate the compositions according to the invention.

EXAMPLE 7

An injectable solution having the following composition is prepared:

| | |
|---|---:|
| 7-[D-α-amino(5,6-dihydro-1,4-dithiin-2-yl)acetamido]-2-carboxy-3-methyl-8-oxo-5-thia-1-aza-bicyclo[4.2.0]oct-2-ene trifluoroacetate | 323.8 mg |

-continued

| | |
|---|---:|
| sodium chloride | 1.5 mg |
| injectable solvent | 2 cc. |

EXAMPLE 8

Tablets having the following composition are prepared in accordance with the usual method:

| | |
|---|---:|
| 7-[DL-α-amino(5,6-dihydro-1,4-dithiin-2-yl)acetamido]-3-methyl-8-oxo-2-pivaloyloxymethoxycarbonyl-5-thia-1-aza-bicyclo[4.2.0]oct-2-ene trifluoroacetate | 336.5 mg |
| starch | 90 mg |
| precipitated silica | 30 mg |
| magnesium stearate | 5 mg. |

We claim:

1. A cephalosporin compound of the formula:

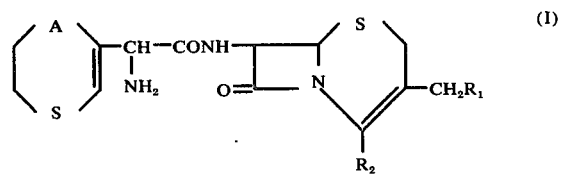

in which A is oxygen or sulphur, $R_1$ is hydrogen or acetoxy and $R_2$ is carboxy or a radical of the formula:

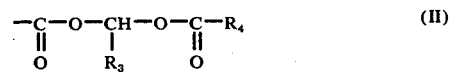

in which the radical

is a radical which can be easily removed enzymatically, and in which $R_3$ is hydrogen or straight or branched chain $C_{1-4}$ alkyl and $R_4$ is straight or branched chain $C_{1-4}$ alkyl or cyclohexyl, its diastereoisomeric forms and mixtures thereof, and its pharmaceutically acceptable salts.

2. A compound according to claim 1 in which A is sulphur, $R_1$ is hydrogen or acetoxy, and $R_2$ is carboxy in the form of a diastereoisomer of a mixture of diastereoisomer.

3. A compound according to claim 1 in which $R_2$ is carboxy.

4. A compound according to claim 1 in which $R_2$ is a radical of the formula (II) as defined in claim 1, its diastereoisomeric forms and mixtures thereof and its pharmaceutically acceptable acid addition salts.

5. A compound according to claim 1, which is 3-acetoxymethyl-7-[DL-α-amino(5,6-dihydro-1,4-dithiin-2-yl)acetamido]-2-carboxy-8-oxo-5-thia-1-aza-bicyclo[4.2.0]oct-2-ene, and its pharmaceutically acceptable salts.

6. A compound according to claim 1, which is 7-[DL-α-amino(5,6-dihydro-1,4-dithiin-2-yl)acetamido]-2-carboxy-3-methyl-8-oxo-5-thia-1-aza-bicyclo[4.2.-0]oct-2-ene, and its pharmaceutically acceptable salts.

7. A compound according to claim 1, which is 7-[D-α-amino(5,6-dihydro-1,4-dithiin-2-yl)acetamido]-2- carboxy-3-methyl-8-oxo-5-thia-1-aza-bicyclo[4.2.0]oct-2-ene, and its pharmaceutically acceptable salts.

8. A compound according to claim 1, which is 7-[DL-α-amino(5,6-dihydro-1,4-oxathiin-2-yl)acetamido]-2-carboxy-3-methyl-8-oxo-5-thia-1-aza-bicyclo[4.2.0]oct-2-ene, and its pharmaceutically acceptable salts.

9. A compound according to claim 1, which is 3-acetoxymethyl-7-[DL-α-amino(5,6-dihydro-1,4-oxathiin-2-yl)acetamido]-2-carboxy-8-oxo-5-thia-1-aza-bicyclo[4.2.0]oct-2-ene, and its pharmaceutically acceptable salts.

10. A compound according to claim 1, which is 7-[DL-α-amino(5,6-dihydro-1,4-dithiin-2-yl)acetamido]-3-methyl-8-oxo-2-pivaloyloxymethoxycarbonyl-5-thia-1-aza-bicyclo[4.2.0]oct-2-ene, and its pharmaceutically acceptable salts.

11. A pharmaceutical composition, which comprises, as active ingredient, a cephalosporin compound as claimed in claim 1, in association with a pharmaceuticaly acceptable carrier, diluent or adjuvant.

12. A pharmaceutical composition, which comprises, as active ingredient, a cephalosporin compound as claimed in claim 3, in association with a pharmaceutically acceptable carrier, diluent or adjuvant.

13. A pharmaceutical composition, which comprises, as active ingredients, a cephalosporin compound as claimed in claim 4, in association with a pharmaceutically acceptable carrier, diluent or adjuvant.

* * * * *